United States Patent
Sugimura

(10) Patent No.: US 7,875,045 B2
(45) Date of Patent: Jan. 25, 2011

(54) CORNEAL INCISION APPARATUS AND BLADE CASE FOR STORING BLADE UNIT TO BE MOUNTED IN THE CORNEAL INCISION APPARATUS

(75) Inventor: Masahiro Sugimura, Aichi-ken (JP)

(73) Assignee: Nidek Co., Ltd., Gamagori-shi (JP)

( * ) Notice: Subject to any disclaimer, the term of this patent is extended or adjusted under 35 U.S.C. 154(b) by 254 days.

(21) Appl. No.: 11/700,869

(22) Filed: Feb. 1, 2007

(65) Prior Publication Data

US 2007/0185509 A1 Aug. 9, 2007

(30) Foreign Application Priority Data

| Feb. 2, 2006 | (JP) | 2006-026409 |
| Feb. 2, 2006 | (JP) | 2006-026410 |
| Sep. 29, 2006 | (JP) | 2006-268676 |

(51) Int. Cl.
*A61F 9/00* (2006.01)
(52) U.S. Cl. .................................................. 606/166
(58) Field of Classification Search .............. 606/166, 606/182, 167, 107, 171, 131–132; 600/463; 30/357
See application file for complete search history.

(56) References Cited

U.S. PATENT DOCUMENTS

| 4,735,203 A * | 4/1988 | Ryder et al. ................. 606/182 |
| 6,165,189 A | 12/2000 | Ziemer |
| 6,302,896 B1 * | 10/2001 | Carriazo et al. ............. 606/166 |
| 6,592,601 B1 | 7/2003 | Toh et al. |
| 6,610,075 B1 | 8/2003 | Levesque et al. |
| 6,623,498 B1 | 9/2003 | Ziemer |
| 2003/0045895 A1 * | 3/2003 | Ross et al. ................... 606/166 |
| 2004/0010277 A1 * | 1/2004 | Levesque et al. ............ 606/166 |
| 2004/0073246 A1 | 4/2004 | Aufaure et al. |
| 2005/0075658 A1 | 4/2005 | Duprat et al. |
| 2006/0229649 A1 | 10/2006 | Levesque et al. |

FOREIGN PATENT DOCUMENTS

| JP | A-2000-237229 | 9/2000 |
| JP | A-2002-528226 | 9/2002 |
| JP | A-2004-130132 | 4/2004 |
| JP | A-2004-528895 | 9/2004 |
| WO | WO 00/25711 | 5/2000 |
| WO | WO0057799 A1 * | 10/2000 |

* cited by examiner

*Primary Examiner*—Anthuan T Nguyen
*Assistant Examiner*—Tin Nguyen
(74) *Attorney, Agent, or Firm*—Oliff & Berridge, PLC

(57) ABSTRACT

A cornea incision apparatus for incising a cornea in a layered form, comprises; a blade unit having a blade for corneal incision; and a cutter head unit arranged to detachably hold the blade unit in such a manner as to allow oscillation thereof, the cutter head unit including; a cavity formed with a first opening which opens to the outside to allow direct mounting/demounting of the blade unit, and arranged to hold the blade unit in such a manner as to allow oscillation thereof; and a first stopper provided in the first opening, the first stopper being movable between a first position for restricting movement of the blade unit in the first opening and a second position for allowing the movement of the blade unit in the first opening.

3 Claims, 15 Drawing Sheets

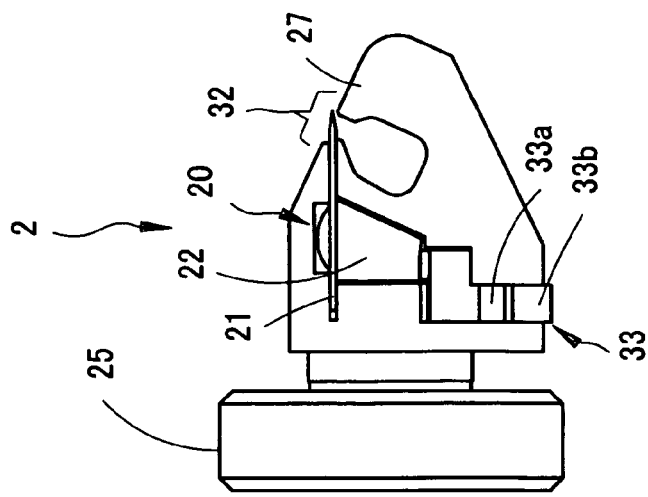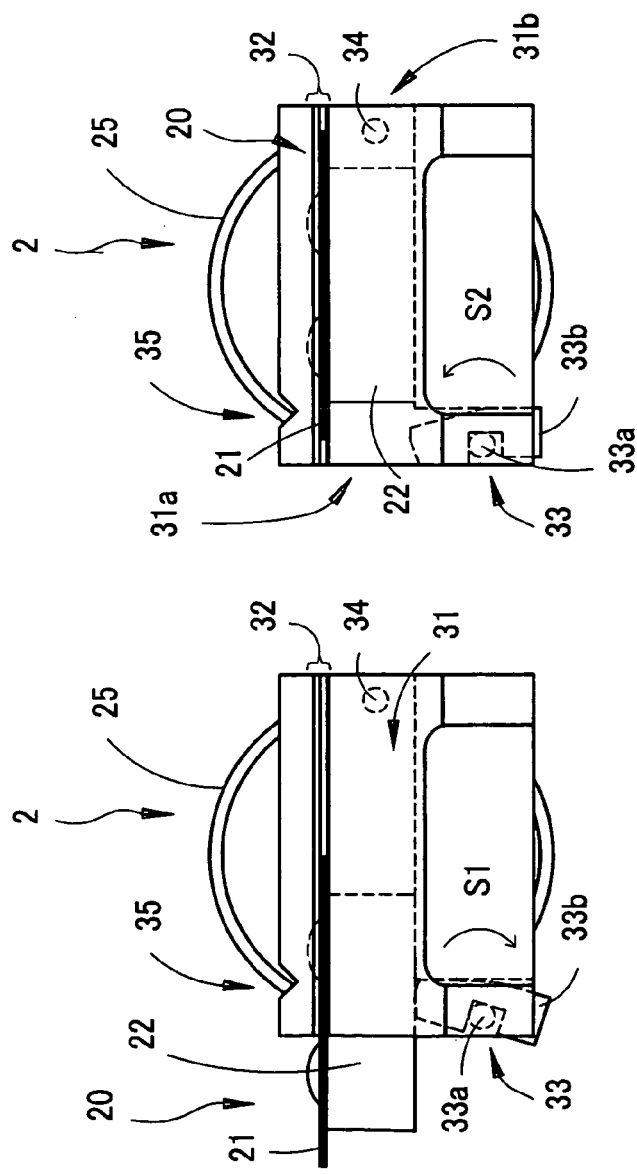

CORNEAL INCISION APPARATUS AND BLADE CASE FOR STORING BLADE UNIT TO BE MOUNTED IN THE CORNEAL INCISION APPARATUS

BACKGROUND OF THE INVENTION

1. Field of the Invention

The present invention relates to a corneal incision apparatus for incising a cornea in a layered form, and a blade case for storing a blade unit which is mounted (loaded) in and used with the corneal incision apparatus.

2. Description of Related Art

As known operative procedures of corneal surgery for ablating part of a cornea by an excimer laser beam or the like, there are a LASIK (laser assisted in-situ keratomileusis) surgery wherein a flap is formed by incising a portion with a thickness of about 150 μm ranging from an epithelium to a midportion of a corneal stroma in a layered form, and an Epi-LASIK (Epithelial LASIK) surgery wherein a flap is formed by incising only an epithelium in a layered form, and others. As a device for incising a cornea in a layered form, a corneal incision apparatus called "keratome" has been used.

The corneal incision apparatus is arranged to incise a cornea in a layered form in such a manner that a suction ring (an apparatus fixing member) is fixed under suction to a portion ranging from a corneal limbus to a conjunctiva, and then a blade is caused to move in the direction of incision while being oscillated at a high speed in the direction of a blade width. The blade is preferably disposable to prevent infection or the like (it also may be reused after sterilization). Accordingly, a technique for facilitating blade replacement has been proposed (see WO 00/25711 (Domestic publication No. 2002-528226)).

Since the blade and a cutter head (a blade holder) which holds the blade are small, it is likely to take the trouble in mounting (attaching) or demounting (detaching) the blade to or from the cutter head. If an operator or an assistant accidentally drops the blade down or strikes the blade on the cutter head during a mounting (attaching) work, the blade will be contaminated or damaged and has to be sterilized or replaced again.

The technique of WO 00/25711 (Domestic publication No. 2002-528226) proposed for facilitating blade replacement is arranged to set a blade in a blade injector after taken out of a blade case storing the blade and mount (attach) the blade to a cutter head by the blade injector. Thus, there is still a risk of dropping the blade down in the process of a mounting (attaching) work (up to engagement of the blade with part of a blade oscillating mechanism in the cutter head).

BRIEF SUMMARY OF THE INVENTION

The present invention has an object to provide a corneal incision apparatus and a blade case which can facilitate replacement of a blade and prevent contamination and damage of the blade.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a cornea incision apparatus for incising a cornea in a layered form, comprising: a blade unit having a blade for corneal incision; and a cutter head unit arranged to detachably hold the blade unit in such a manner as to allow oscillation thereof, the cutter head unit including; a cavity formed with a first opening which opens to the outside to allow direct mounting/demounting of the blade unit, and arranged to hold the blade unit in such a manner as to allow oscillation thereof; and a first stopper provided in the first opening, the first stopper being movable between a first position for restricting movement of the blade unit in the first opening and a second position for allowing the movement of the blade unit in the first opening.

According to another aspect of the present invention, a blade case for storing a blade unit having a blade for corneal incision, the blade unit being configured to be mounted in and used with a corneal incision apparatus for incising a cornea in a layered form, the blade case comprising: a cavity formed with a first opening which opens to the outside to allow direct ejection of the blade unit, and arranged to hold the blade unit.

BRIEF DESCRIPTION OF THE DRAWINGS

FIGS. 4A, 4B, and 4C are views showing a schematic configuration and an operation of a stopper of the cutter head unit.

DETAILED DESCRIPTION OF THE PREFERRED EMBODIMENTS

Figure 1:
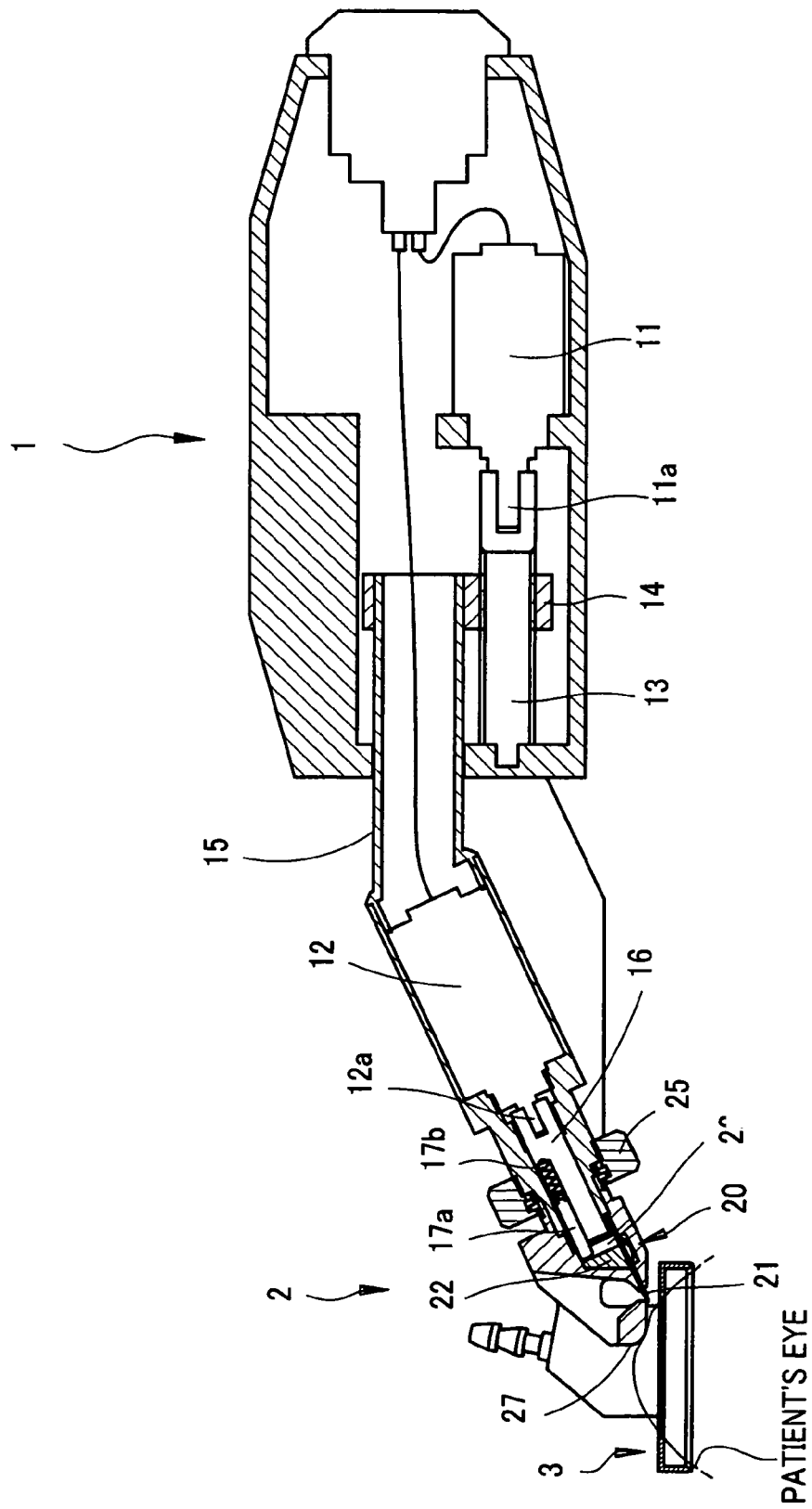
FIG. 1 is a schematic configuration view of a corneal incision apparatus of a preferred embodiment of the present invention.
Figure 2:
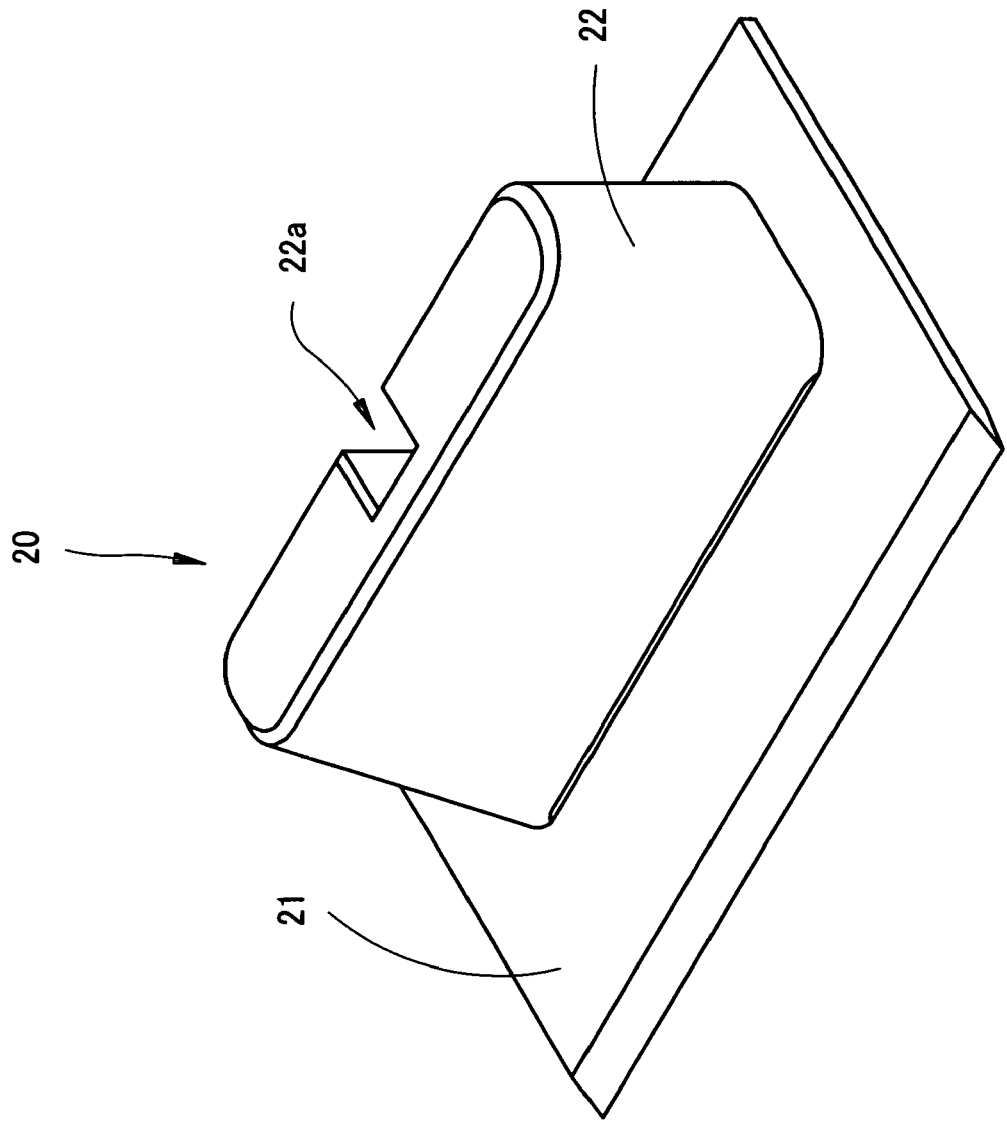
FIG. 2 is a schematic configuration view of a blade unit having a blade for corneal incision.

A detailed description of a preferred embodiment of the present invention will now be given referring to the accompanying drawings. FIG. 1 is a schematic configuration view of a corneal incision apparatus of the present embodiment of the present invention.

A main body 1 of the corneal incision apparatus comprises a cutter head unit 2 serving as a blade holder unit for holding a blade unit 20 for corneal incision so that the blade unit 20 is mountable/demountable (attachable/detachable) and allowed to oscillate, and a suction ring unit 3 for fixing the apparatus on a patient's eye (an operative eye). The suction ring 3 is fixed under suction to an area of the patient's eye ranging from a corneal limbus to a conjunctiva.

In the present embodiment, the blade unit 20 is arranged to be replaceable, and besides, the cutter head unit 2 removably attached to the main body 1 may also be arranged to be replaceable.

The blade unit 20 includes a blade 21 for corneal incision and an oscillation transmitting member 22 fixedly attached on the blade 21. The blade 21 is any one having a sharp blade edge, such as a metallic blade, a mineral blade, a resinous blade, a ceramic blade. The oscillation transmitting member 22 is made of a material such as resin easy to make.

In the main body 1, a translation motor 11 is fixedly installed for rectilinearly moving the cutter head unit 2 on the suction ring unit 3 in an incising direction. A rotating shaft 11*a* of the motor 11 is fixedly connected to a rear end of a translation screw 13 with a threaded portion having a length corresponding to a distance that permits the cutter head unit 2 to move. A front end of the translation screw 13 is connected to the main body 1. A joint member 14 threadably mounted on the translation screw 13 is fixedly connected to a rear end of a coupling member 15 that couples the main body 1 with the cutter head unit 2. With such structure, as the motor 11 is rotated forward or reversely, the coupling member 15 moves forward and backward in the direction of axes of the rotating shaft 11*a* and the translation screw 13 through the translation screw 13 and the joint member 14, thereby causing the cutter head unit 2 coupled with a front end of the coupling member 15 to move forward and backward in the same direction.

In the coupling member 15, an oscillation motor 12 is fixedly installed for oscillating the blade unit 20 (the blade 21) in a blade width direction at a high speed. A rotating shaft 12*a* of the motor 12 is fixedly connected to a rear end of a rotating shaft 16 so as to be rotatably held in the coupling member 15. Further, an eccentric pin 17*a* is embedded, together with a spring 17*b*, on a front end of the rotating shaft 16 at a position offset from the center of rotation.

The cutter head unit 2 is fixedly attached to the coupling member 15 with a nut 25. This fixedly attaching causes the eccentric pin 17*a* to engage in the blade unit 20 having been mounted in the cutter head unit 2 prior to the fixedly attaching to the coupling member 15. Alternatively, the blade unit 20 is mounted in the cutter head unit 2 after the fixedly attaching to the coupling member 15 and thus engaged with the eccentric pin 17*a*. The eccentric pin 17*a* is arranged to be retracted (inserted) into the rotating shaft 16 by the spring 17. Accordingly, at the time of fixedly attaching of the cutter head unit 2 or mounting of the blade unit 20, a distal end of the eccentric pin 17*a* comes into engagement with a vertical groove 22*a* of the oscillation transmitting member 22. With such structure, the rotating shaft 16 is rotated as the motor 12 is rotated, circularly moving the eccentric pin 17*a* embedded in the rotating shaft 16, thereby causing the blade unit 20 engaged with the eccentric pin 17*a* to oscillate in the blade width direction perpendicular to the axial direction.

The blade unit 20 is held in the cutter head unit 2 so that the blade 21 is at a predetermined angle (e.g., 25 degrees) with respect to the horizontal plane.

The cutter head unit 2 is provided at its lower front part with an applanator (an applanation part) 27 to flatly applanate a cornea of a patient's eye in advance of the blade 21 as the cutter head unit 2 is moved forward.

Figure 3A:
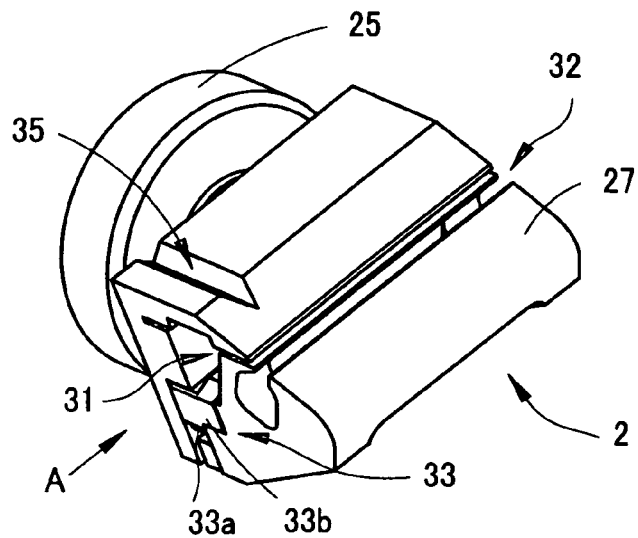
FIGS. 3A, 3B, and 3C are schematic configuration views of a cutter head unit.
Figure 3B:
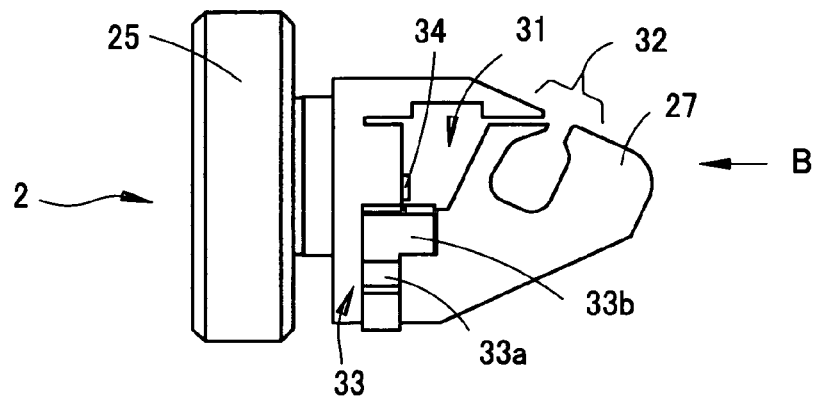
Figure 3C:
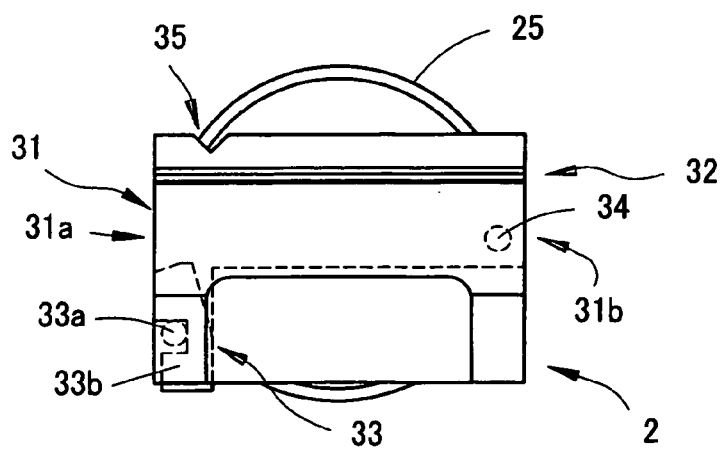

FIG. 3A is an oblique perspective view of the cutter head unit 2 in which the blade unit 20 is not mounted. FIG. 3B is a side view seen from a direction of an arrow A in FIG. 3A. FIG. 3C is a perspective view seen from a direction of an arrow B in FIG. 3B. Regarding the apparatus of the present embodiment, mounting/demounting of the blade unit 20 with respect to the cutter head unit 2 is conducted after turning the apparatus (the cutter head unit 2) upside down in order to make the blade edge of the blade 21 easy to view. All the subsequent figures are therefore illustrated in the upside-down state. The mounting/demounting of the blade unit 20 with respect to the cutter head unit 2 may be conducted without turning the apparatus (the cutter head unit 2) upside down.

The cutter head unit 2 is formed with a cavity (a blade unit holding part) 31 having a shape of substantially the same section as that of the blade unit 20 so that the blade unit 20 is insertable from the direction of the arrow A. When the blade unit 20 is inserted in the cavity 31, the blade edge of the blade 21 will protrude from a slot (opening) 32. In an opening 31*a* of the cavity 31 on an insertion side, a movable stopper 33 is provided for preventing (restricting) the blade unit 20 from dropping or coming off (moving). In an opposite opening 31*b*, similarly, a fixed stopper 34 is provided for preventing (restricting) the blade unit 20 from dropping or coming off (moving). Further, the cutter head unit 2 is provided with a notch-shaped mating part 35 on a rearward bottom, which is engageable with a mating part 55 of a blade case 50 mentioned later (the details will be mentioned later).

FIG. 4A is a perspective view seen from the same direction as in FIG. 3C, showing the blade unit 20 being inserted halfway into the cavity 31. FIG. 4B is a perspective view seen from the same direction as in FIG. 4A, showing the blade unit 20 being completely inserted. FIG. 4C is a side view seen from the same direction as in FIG. 3B, showing the blade unit 20 being completely inserted.

The stopper 33 includes a pin 33*a* fixed to the cutter head unit 2 and a move member 33*b* attached to the pin 33*a* so as to be movable in directions of arrows S1 and S2. The move member 33*b* is movably held between the pin 33*a* and a side surface of the cutter head unit 2. As shown in FIGS. 3B and 3C, in which the blade unit 20 is not inserted, part of the move member 33*b* is allowed to protrude into the cavity 31. When this protruding portion is pushed down from the outside (by pressure exerted thereon in the direction of the arrow S1), the move member 33*b* is swung (inclined) about the pin 33*a* in the direction of the arrow S1 and then no longer protrudes into the cavity 31. In this state, as shown in FIG. 4A, the blade unit 20 is permitted to go into the cavity 31. After the blade unit 20 is completely inserted in the cavity 31, when the move member 33*b* is pushed up from the outside (by pressure exerted thereon in the direction of the arrow S2), the move member 33*b* is swung (inclined) about the pin 33*a* in the direction of the arrow S2 to protrude into the cavity 31 again. In this state, as shown in FIGS. 4B and 4C, the blade unit 20 can be prevented from dropping off the cavity 31. Further, when the cutter head unit 2 is returned from the upside-down state to the original state, the move member 33*b* comes down by its own weight and further protrudes into the cavity 31.

As shown in FIGS. 4A and 4B, the move member 33*b* has a non-right-angled (slanted) section on the side closer to the mating part 35 and a substantially right-angled section on the opposite side. Accordingly, even when the move member 33*b* is pushed from the inside by the blade unit 20 due to inclination or the like of the cutter head unit 2, the move member 33*b* protruding into the cavity 31 will not be inclined to the outside of the cutter head unit 2.

It should be noted that the move member 33*b* may be adapted to simply swing (incline) in the directions of the arrows S1 and S2 or to move up and down instead of swinging. The move member 33b of the stopper 33 may be adapted to be pushed up to return to its original position by an urging member such as a spring and a rubber member, thus protruding into the cavity 31 again. The move member 33b may also be adapted to come down by its own weight to protrude into the cavity 31 again without being pushed up when the cutter head unit 2 is returned from the upside-down position to the original position.

Figure 5A:
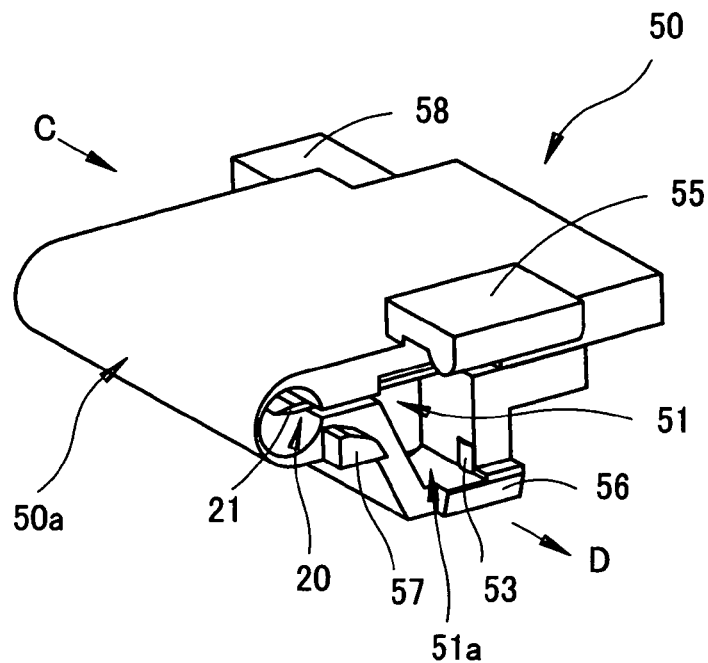
FIGS. 5A and 5B are schematic configuration views of a blade case.
Figure 5B:
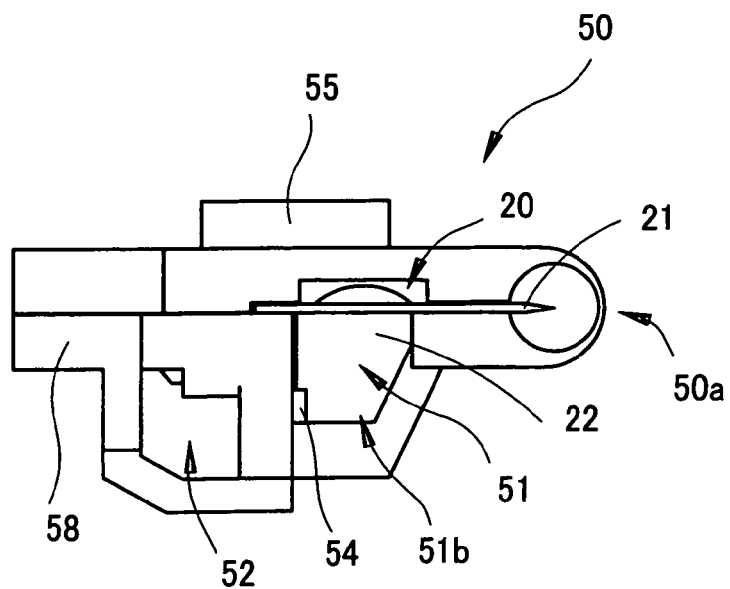

The following explanation is made on the blade case 50 for storing the blade unit 20 in the preferred embodiment of the present invention. FIG. 5A is an oblique perspective view of the blade case 50 in which the blade unit 20 is stored. FIG. 5B is a side view seen from a direction of an arrow C in FIG. 5A. The blade case 50 in the present embodiment is arranged to open and close about a hinge portion 50a (FIGS. 5A and 5B show a closed state). When the blade unit 20 is to be stored in the blade case 50 (for assembling or mounting), the blade case 50 is opened about the hinge portion 50a to store the blade unit 20 in a cavity 51 and then closed. This configuration makes it easy to store the blade unit 20 in the blade case 50. Such blade case 50 is preferably made of transparent resin or the like to the extent that the blade unit 20 internally stored is visually check.

The blade case 50 is formed with the cavity (a blade unit storing part) 51 having a shape of substantially the same section as that of the blade unit 20 so that the blade unit 20 is ejectable in a direction of an arrow D. The blade case 50 is formed with a cavity (a push rod storing part) 52 in which a push rod 59 mentioned later is inserted and stored. In an opening 51a of the cavity 51 on an ejection side, a fixed small stopper 53 is provided for preventing (restricting) the blade unit 20 from dropping or coming off (moving). In an opposite opening 51b, similarly, a fixed stopper 54 is provided for preventing (restricting) the blade unit 20 from dropping or coming off (moving). The small stopper 53 is designed to be so large as to prevent the blade unit 20 from dropping off by its own weight (several hundreds milligrams) when the blade case 50 is inclined. However, if a certain degree of external force is applied to the blade unit 20, the blade unit 20 can go over the small stopper 53 and be ejected from the cavity 51. This external force is the force exerted by the push rod 59 mentioned later.

The blade case 50 includes, at its top on the ejection side, the hook-shaped mating part 55 engageable with the mating part 35 of the cutter head unit 2. The blade case 50 includes, at its bottom on the ejection side, a pressing part 56 which pushes down the move member 33b of the cutter head unit 2. A guide part 57 engageable with the slot 32 of the cutter head unit 2 is provided obliquely above the pressing part 56. The blade case 50 further includes a grip 58.

Figure 6A:
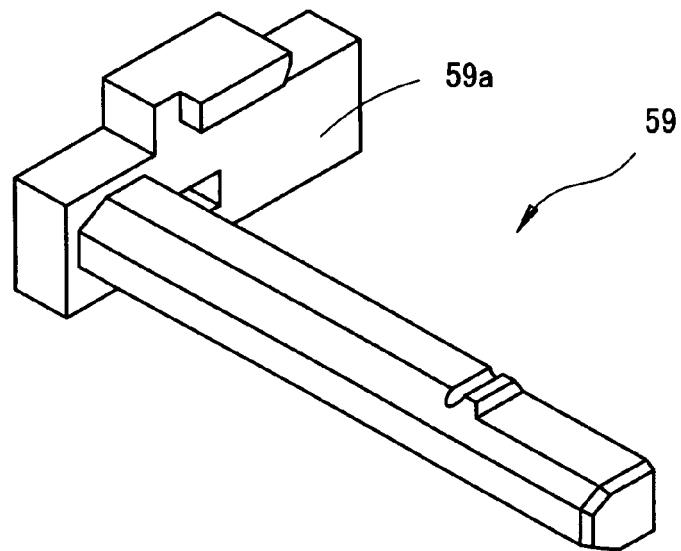
FIGS. 6A and 6B are schematic configuration views of the blade case.
Figure 6B:
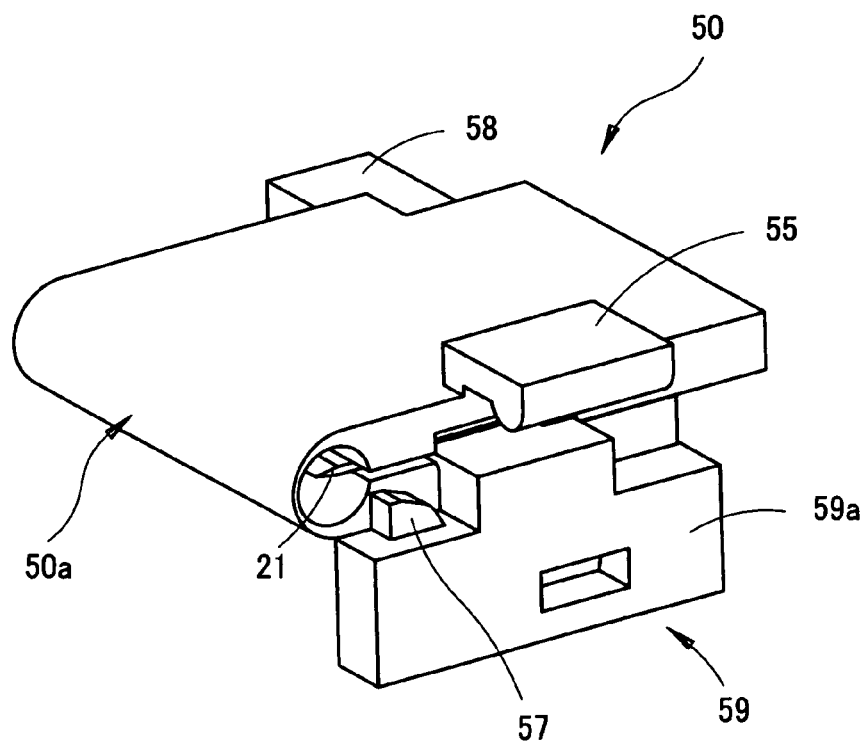

FIG. 6A is an oblique perspective view of the push rod 59 which is inserted and stored in the blade case 50. FIG. 6B is an oblique perspective view of the blade case 50 with the push rod 59 inserted and stored, seen from the same direction as in FIG. 5A. The push rod 59 has a grip 59a and is of a cross section shaped to insert into the cavity 51 of the blade case 50 through the opening 51b and also of a cross section shaped to insert into the cavity 31 of the cutter head unit 2 through the opening 31b. When the push rod 59 is inserted and stored in the cavity 52, the grip 59a is also used as a cover (a stopper) for the opening 51a of the cavity 51 on the ejection side (where the small stopper 53 exists) as shown in FIG. 6B. Further, the blade case 50 and the push rod 59 are configured to prevent the push rod 59 inserted in the cavity 52 from easily coming off. For example, they may be adapted to allow the rod portion of the push rod 59 to fit in the cavity 52.

Figure 7A:
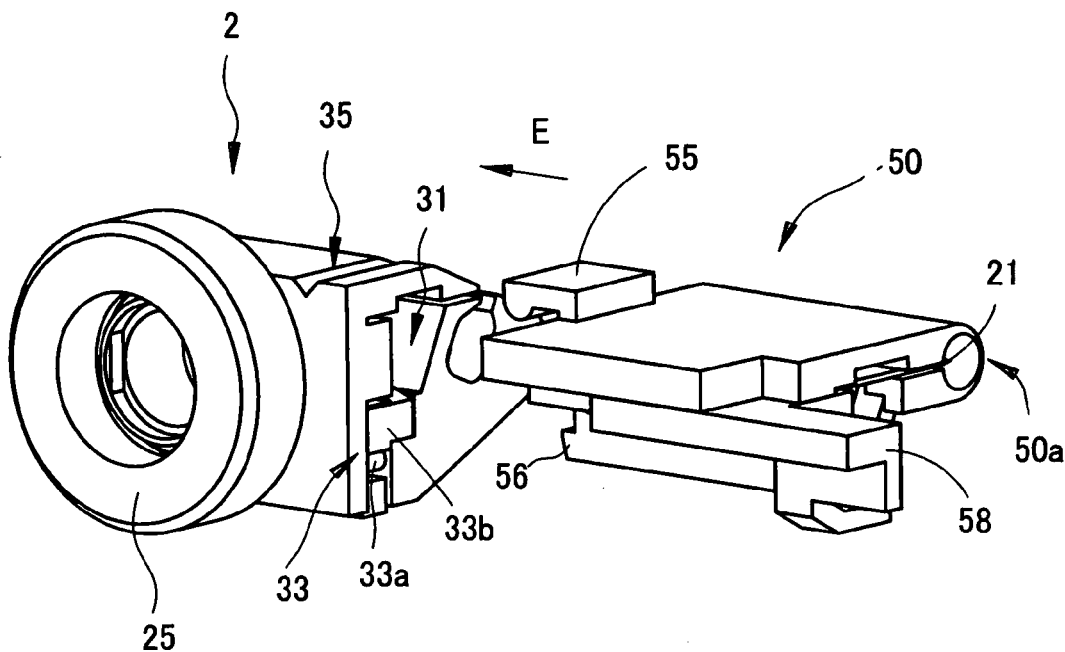
FIGS. 7A and 7B are views showing operations to mount the blade unit from the blade case to the cutter head unit.
Figure 7B:
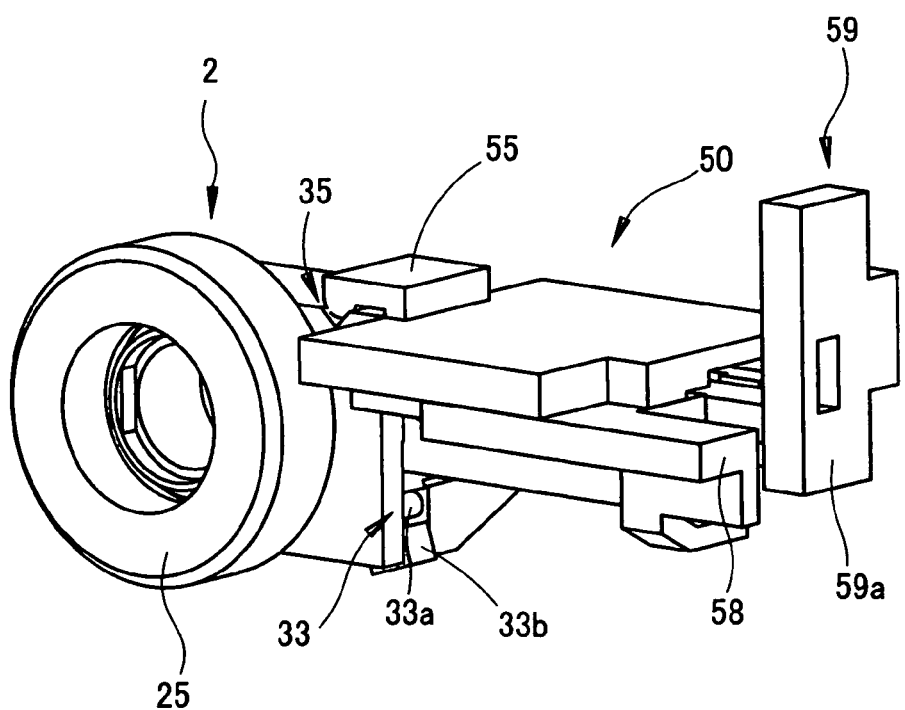

The following explanation is made on an operation to mount the blade unit 20 from the blade case 50 to the cutter head unit 2. FIG. 7A is a view showing a state where the blade case 50 is not yet attached (connected) to the cutter head unit 2. FIG. 7B is a view showing an attached (connected) state.

The push rod 59 inserted and stored in the blade case 50 is first removed therefrom. The blade case 50 is oriented so that its ejection side where the mating part 55 exists faces the cutter head unit 2. The blade case 50 is moved in a direction of an arrow E to bring the mating part 55 into engagement with the mating part 35 of the cutter head unit 2. Accordingly, the pressing part 56 of the blade case 50 pushes down the move member 33b of the cutter head unit 2 in the direction of the arrow S1. The guide part 57 of the blade case 50 is engaged in the slot 32 of the cutter head unit 2. Thus, the cavity 51 of the blade case 50 is placed in alignment with the cavity 31 of the cutter head unit 2.

As shown in FIG. 7B, the push rod 59 is then inserted into the cavity 51 of the blade case 50 through the opening 51b, thereby pushing the blade unit 20 out of the cavity 51 into the cavity 31 of the cutter head unit 2. The move member 33b of the cutter head unit 2 has been pressed down and thus the blade unit 20 is inserted into the cavity 31. After the blade unit 20 is completely inserted in the cavity 31, the blade case 50 is detached from the cutter head unit 2. This removes pressure of the pressing part 56 on the move member 33b, allowing the move member 33b to move up in the direction of the arrow S2. Thus, part of the move member 33b protrudes into the cavity 31, thereby preventing the blade unit 20 inserted and held in the cavity 31 from dropping off the cavity 31.

Figure 8:
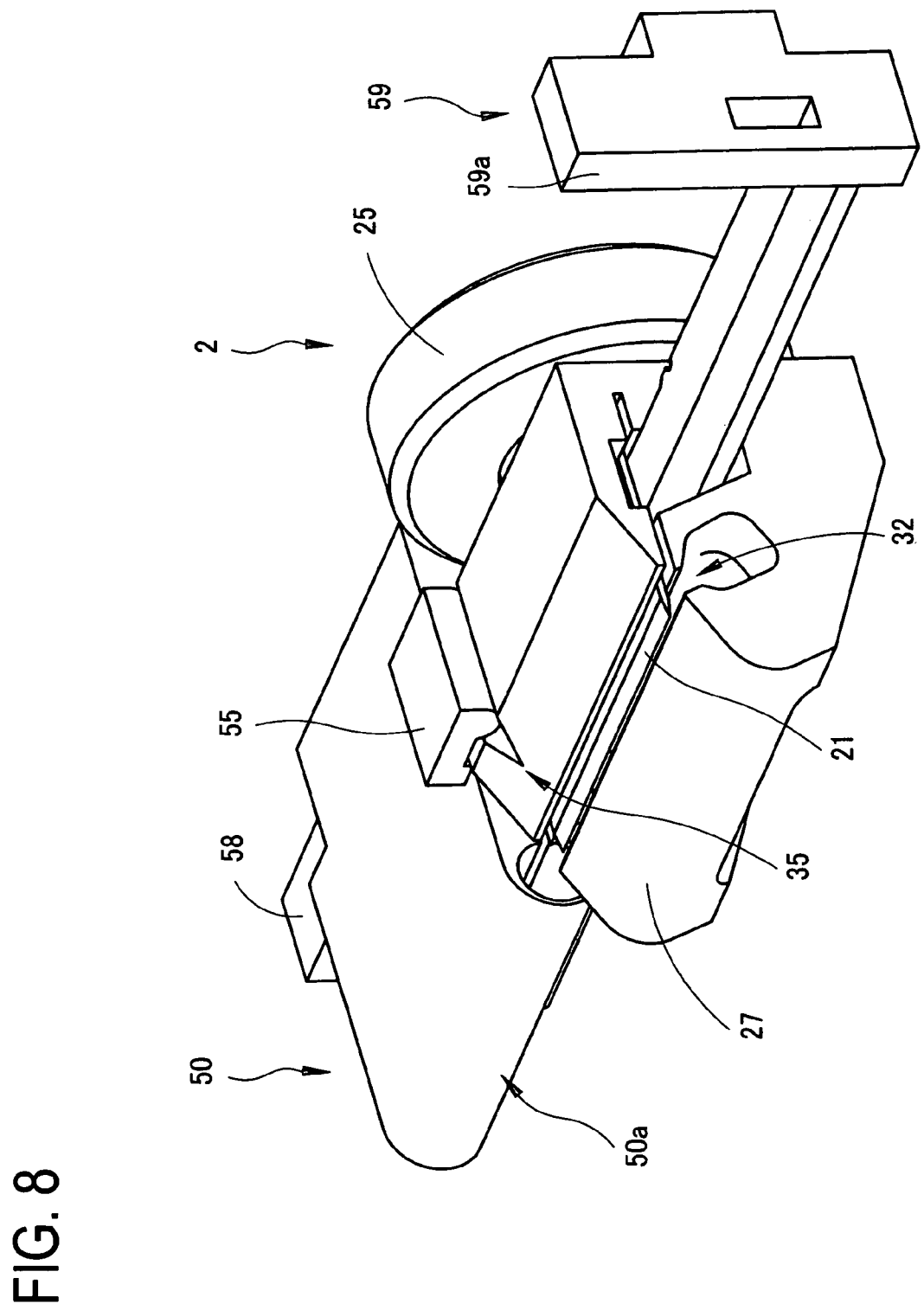
FIG. 8 is a view showing an operation to return the blade unit from the cutter head unit to the blade case.

After use, the blade unit 20 is replaced with new one. FIG. 8 is a view showing an operation to return the blade unit 20 from the cutter head unit 2 into the blade case 50. Ejection of the blade unit 20 is performed in opposite procedures to those for insertion of the blade unit 20. When the blade case 50 is attached (connected) to the cutter head unit 2, pressing down the move member 33b, the push rod 59 is inserted into the cavity 31 through the opening 31b, thereby pushing the blade unit 20 out of the cavity 31 into the cavity 51 of the blade case 50.

As above, without directly touching the blade unit 20, it can be transferred directly from the blade case 50 into the cutter head unit 2 and also returned directly from the cutter head unit 2 into the blade case 50. Thus, the blade unit 20 can be replaced readily and prevented from becoming contaminated and damaged. The blade case 50 storing the used blade unit 20 returned thereto will be directly disposed of. It is therefore hygienic and safety.

Figure 9A:
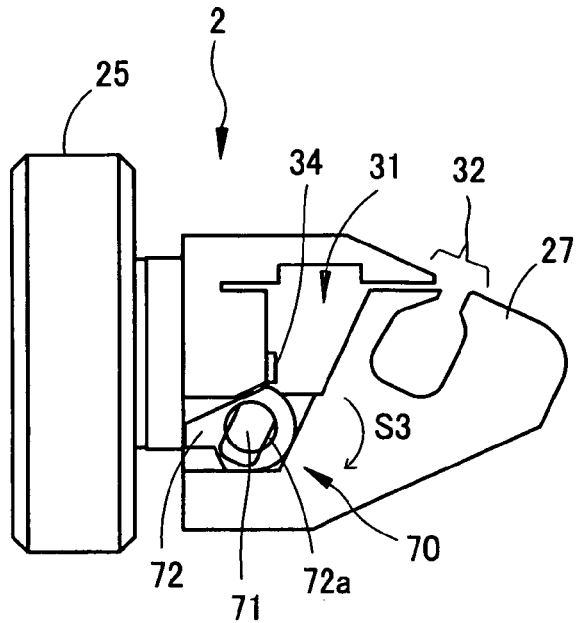
FIGS. 9a and 9B are views showing a schematic configuration and an operation of a modified form of the stopper of the cutter head unit.
Figure 9B:
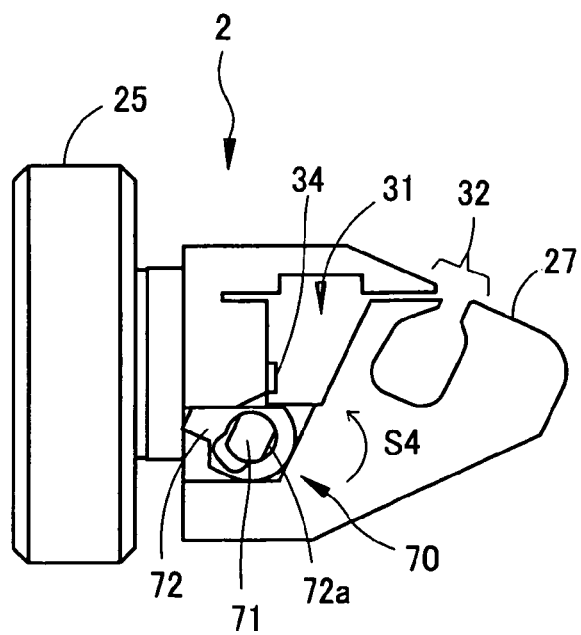

A modified form of the stopper of the cutter head unit will be explained below. FIGS. 9A and 9B are side views of the cutter head unit 2 of the modified form seen from the same direction as in FIG. 3B. In the opening 31a of the cavity 31, a movable stopper 70 is provided for preventing (restricting) the blade unit 20 from dropping or coming off (moving). The stopper 70 includes a pin 71 fixed to the cutter head unit 2 and a move member 72 attached to the pin 71 so as to be movable in directions of arrows S3 and S4.

As shown in FIG. 9A, in which the blade unit 20 is not inserted, part of the move member 72 is allowed to protrude into the cavity 31, thereby preventing the blade unit 20 from dropping off. When this protruding portion is pushed down (by pressure exerted thereon in the direction of the arrow S3), the move member 72 is rotated (inclined) about the pin 71 in the direction of the arrow S3 and then no longer protrudes into the cavity 31 as shown in FIG. 9B. In this way, the blade unit 20 can be inserted into the cavity 31 and reversely be ejected from the cavity 31. On the other hand, when the move member 72 is pushed up (by pressure exerted thereon in the direction of the arrow S4) from a state of FIG. 9B to rotate (incline) in the direction of the arrow S4, it is returned to a state of FIG. 9A.

The pin 71 is of a substantial oval shape. The move member 72 is formed with an aperture 72a having a recess in which the pin 71 can be fitted. Accordingly, when the cutter head unit 2 shown in FIG. 9A is returned from the upside-down state to the original state, the move member 72 comes down by its own weight and further protrudes into the cavity 31. Thus, the pin 71 becomes engaged in the recess of the aperture 72a of the move member 72, which holds the move member 72 against rotation.

When the move member 72 is to be pushed down (rotated in the direction of the arrow S3), fingers, tweezers, or the like are used. It should be noted that the move member 72 may be pushed down in such a manner that the blade case 50 is attached (connected) to the cutter head unit 2. When the move member 72 is to be pushed up (rotated in the direction of the arrow S4), fingers, tweezers, or the like are used. Alternatively, it may be pushed up by an urging member such as a spring and a rubber member. The move member 72 may be configured to move up by its own weight, without being pushed up, as the cutter head unit 2 is returned from the upside-down state to the original state.

Figure 10:
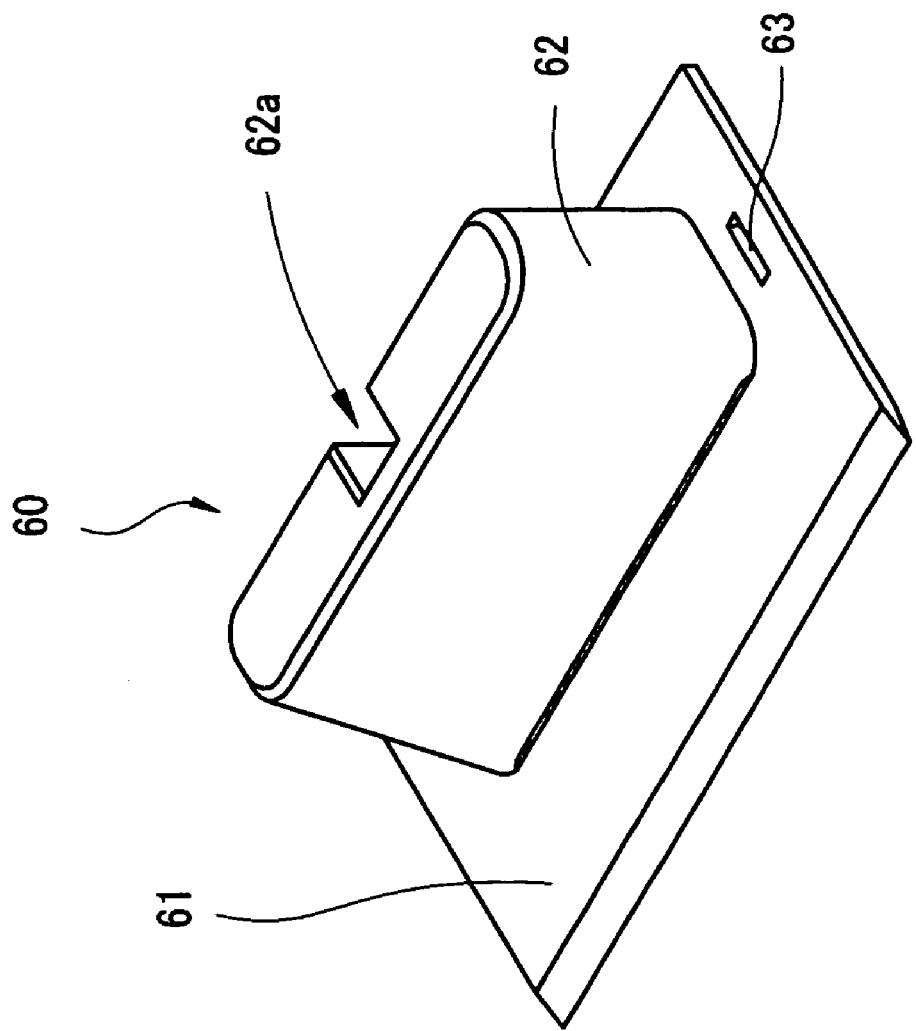
FIG. 10 is a schematic configuration view of a modified form of the blade unit.

A modified form (a second embodiment) of the blade case of the present invention will be explained below. A blade unit 60 of the second embodiment includes, as shown in FIG. 10, a blade 61 for corneal incision and an oscillation transmitting member 62 fixedly attached to the blade 61. The blade 61 and the oscillation transmitting member 62 are made of similar materials as those of the blade unit 20. As with that of the blade unit 20, the oscillation transmitting member 62 is formed with a vertical groove 62a with which the distal end of the eccentric pin 17a is brought into engagement. The blade 61 is of a thickness of about 0.3 mm, a lateral width (blade width) of about 12 mm, and a depth of about 8 mm, which are equal to those of the blade 21. The blade 61 is provided with a notch-shaped mating part 63 with which a mating part 96 of a blade case 80 mentioned later is engageable (the detail will be mentioned later).

Figure 11A:
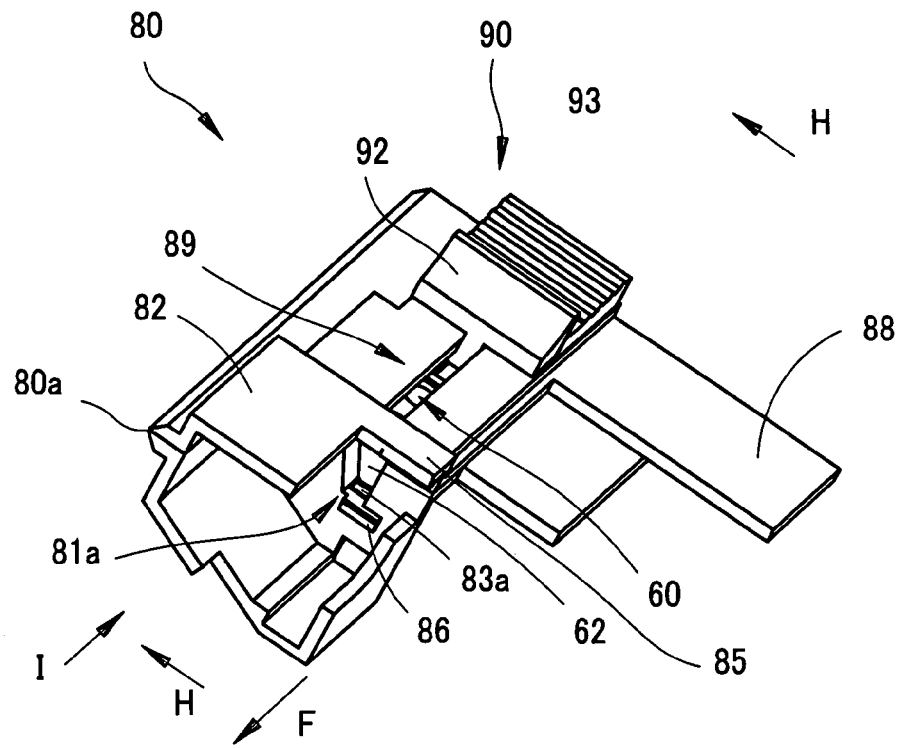
FIGS. 11A and 11B are schematic configuration views of a modified form of the blade case.
Figure 11B:
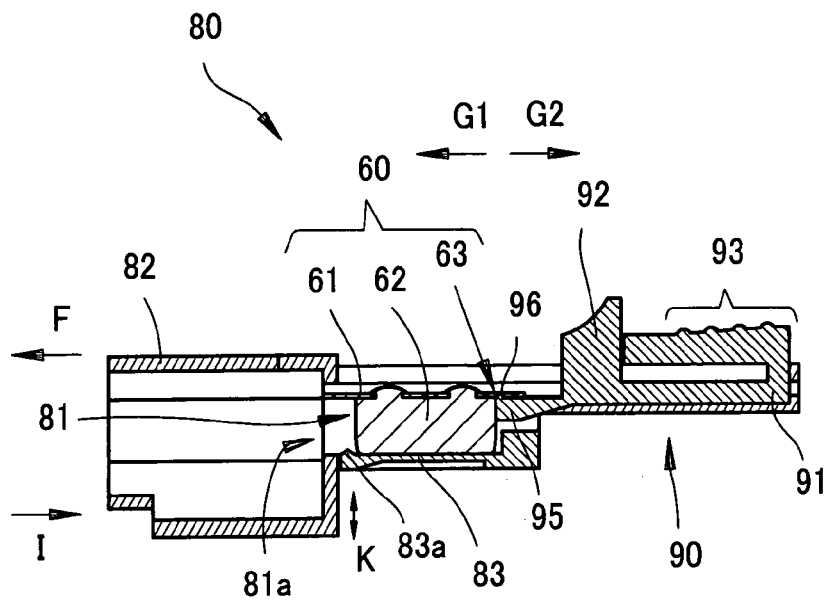

FIG. 11A is an oblique perspective view of the blade case 80 of the second embodiment, showing the state where the blade unit 60 is stored. FIG. 11B is a sectional view seen from a direction of an arrow H in FIG. 11A.

Figure 12A:
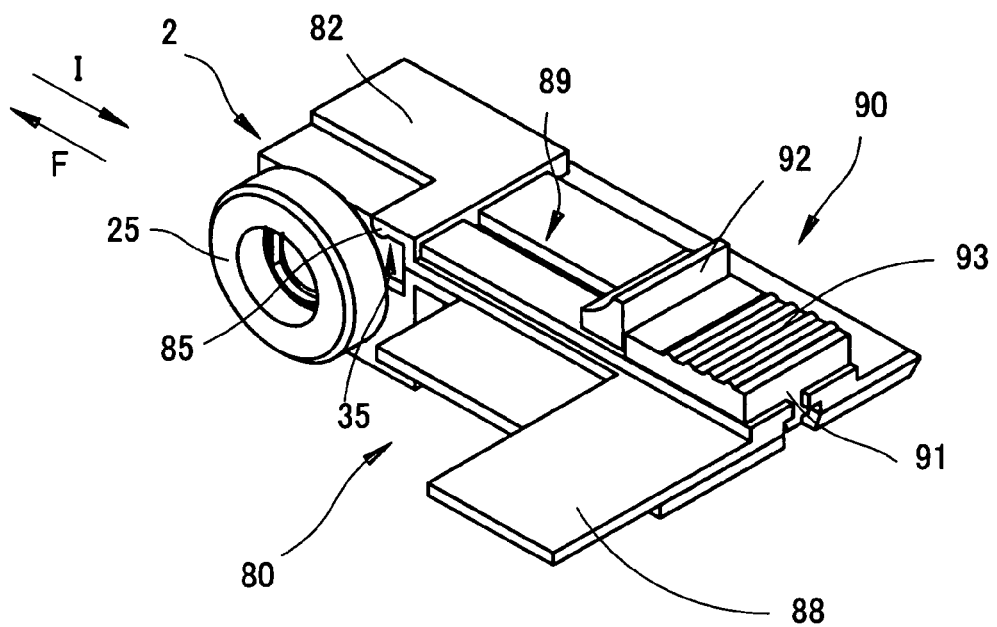
FIGS. 12A and 12B are views showing an operation to mount the modified form of the blade unit from the modified form of the blade case to the cutter head unit.
Figure 12B:
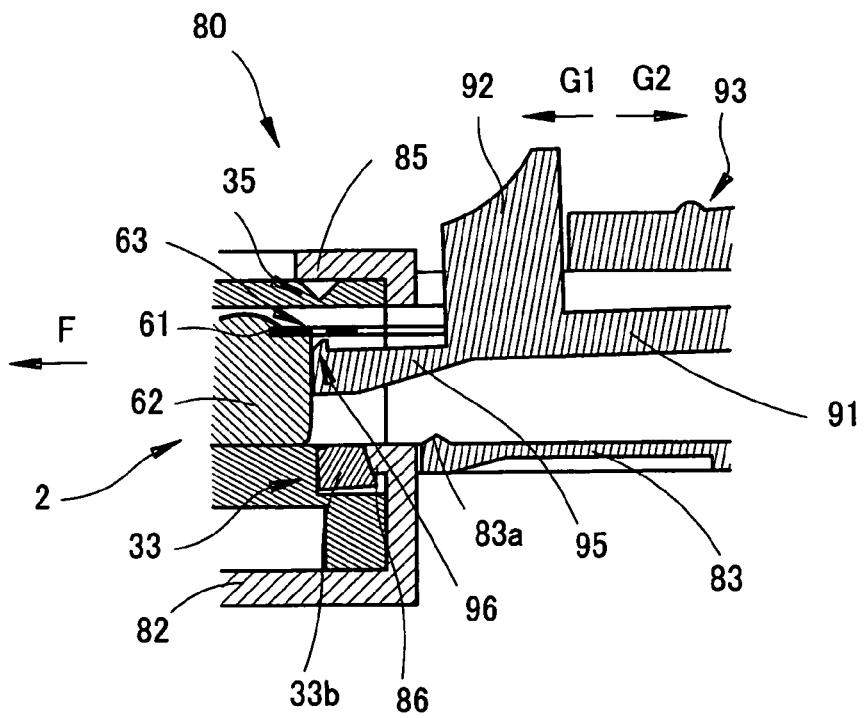
Figure 13A:
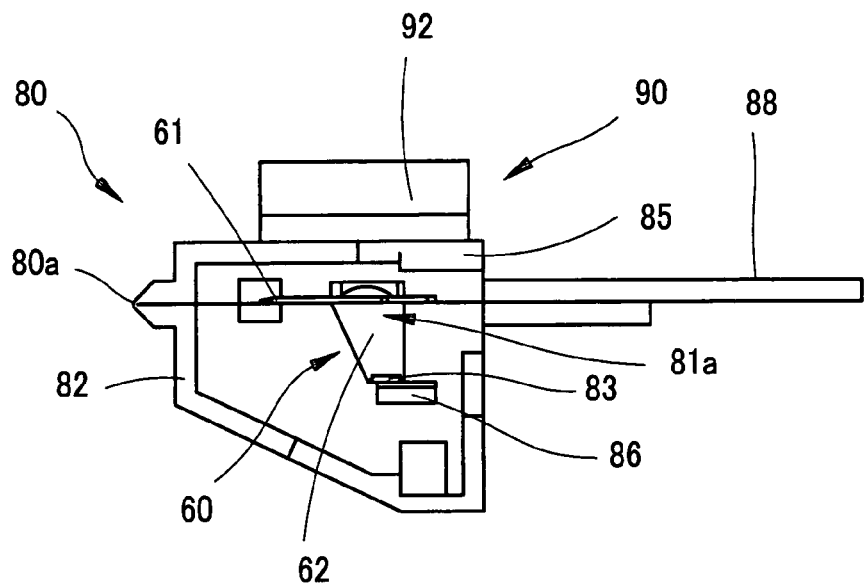
FIGS. 13A and 13B are schematic configuration views of the modified form of the blade case.
Figure 13B:
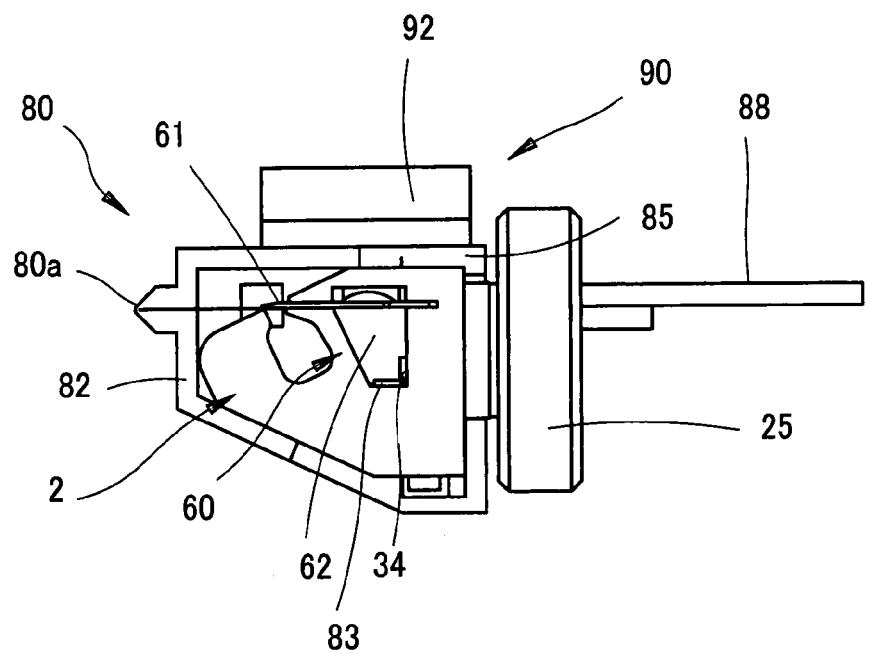

FIG. 12A is a view showing a state where the blade case 80 is attached (connected) to the cutter head unit 2. FIG. 12B is an enlarged sectional view showing a state where the blade unit 60 is inserted halfway from the blade case 80 into the cutter head unit 2, seen from the same direction as in FIG. 11B. FIG. 13A is a side view of the blade case 80 seen from a direction of an arrow I in FIG. 11A. FIG. 13B is a side view showing a state where the blade case 80 is attached (connected) to the cutter head unit 2, seen from the same direction as in FIG. 13A.

The blade case 80 is formed, as with the blade case 50, with a cavity (a blade unit storing part) 81 having a shape of substantially the same section as that of the blade unit 60 so as to store therein the blade unit 60 and eject therefrom the blade unit 60 in a direction of an arrow F. Outside of an opening 81a of the cavity 81 on the ejection side, an attaching part 82 is provided for attachment of the cutter head unit 2. The attaching part 82 is partly formed with a hook-shaped mating part 85 engageable with the mating part 35 of the cutter head unit 2.

The blade case 80 includes a push member 90 slidable in directions of arrows G1 and G2. The push member 90 includes a U-shaped base 91a, a non-flat grip surface 93 with ribs on the upper part of the base 91, a push part (a push rod) 95 formed in the lower part of the base 91 closer to the attaching part 82, and a pressing part 92 formed in the lower part of the base 91 to push down the push part 95.

In the upper part of the blade case 80, a guide groove 89 is formed extending perpendicular to the opening 81a. The lower part of the base 91 is shaped to engage in the guide groove 89 along which the push member 90 is movable in the directions of the arrows G1 and G2. The push part 95 is of a cross section shaped to insert into the cavity 31 of the cutter head unit 2.

The push part 95 is provided at its upper end with the hook-shaped mating part 96 engageable with the mating part 63 of the blade 61. By engagement of the mating parts 63 and 96, the blade 61 (the blade unit 60) is locked. In the state where the blade unit 60 is stored in the blade case 80, the blade unit 60 is locked by the push part 95.

The blade case 80 is formed, in the lower part on the ejection side, with a pressing part 86 for pushing down the move member 33b of the cutter head unit 2, as with the pressing part 56 of the blade case 50. Further, numeral 88 denotes a grip 88, and 80a denotes a hinge portion. The grip 88 and the hinge portion 80a serve as in the same manner as the grip 58 and the hinge portion 50a of the blade case 50.

In the opening 81a of the cavity 81 on the ejection side, a stopper 83 is provided for preventing (restricting) the blade unit 60 from dropping or coming off (moving). The stopper 83 is resilient and formed with a protrusion 83a at the tip. The tip portion of the stopper 83 including the protrusion 83a is flexible in a direction of an arrow K. The blade unit 60 (the oscillation transmitting member 62) stored in the cavity 81 is locked by the protrusion 83a. The stopper 83 has so resiliency as to prevent the blade unit 60 from dropping by its own weight (several hundreds milligrams) when the blade case 50 is inclined. However, if a certain degree of external force is applied to the blade unit 60, the blade unit 60 can go over the stopper 83 and be ejected out of the cavity 81. This external force is the force exerted by the push member 90 or the like.

When the blade unit 60 is to be inserted from the blade case 80 into the cutter head unit 2, the blade case 80 is attached (connected) to the cutter head unit 2. In this case, the cooperation between the shape of the attaching part 82 and the shape of the cutter head unit 2 brings the cavity 81 (the opening 81a) of the blade case 80 into alignment with the cavity 31 (the opening 31a) of the cutter head unit 2. Further, the mating part 85 is engaged with the mating part 35. The pressing part 86 serves to release movement restriction imposed by the stopper 33. When the push member 90 is moved in the direction of the arrow G1, the blade unit 60 is pushed out of the cavity 81 of the blade case 80 into the cavity 31 of the cutter head unit 2. After the blade unit 60 is inserted in the cutter head unit 2 (the cavity 31), the pressing part 92 is depressed to disengage the mating part 96 from the mating part 63, and the push member 90 is moved back in the direction of the arrow G2.

When the blade unit 60 is to be returned from the cutter head unit 2 to the blade case 80, the blade case 80 is attached (connected) to the cutter head unit 2 in the same manner as at the time of insertion, the push member 90 is moved forward in the direction of the arrow G1, and the pressing part 92 is pushed down, thereby bringing the mating part 96 into engagement with the mating part 63 again. When the push member 90 is moved back in the direction of the arrow G2, the blade unit 60 is pulled out of the cavity 31 of the cutter head unit 2 and returned into the cavity 81 of the blade case 80.

As above, the blade case 80 of the second embodiment is integrally provided with the push rod (the push part 95) for pushing the blade unit 60 and besides the push rod is formed with an engagement part engageable with the blade unit 60. Accordingly, moving the push member 90 causes the blade unit 60 to be mounted in and demounted from the cutter head unit 2. This makes it possible to save the trouble in detaching the push rod from the blade case or the like, resulting in improved operationality. It is further possible to prevent dropping of the push rod and hence contamination thereof.

The second embodiment explains as above the configuration that the mating part 96 serving as an engagement part formed in the end of the push part 95 closer to the attaching part 82 is engaged with the mating part 63 of the blade unit 60 to pull the blade unit 60 out of the cutter head unit 2 to return into the blade case 80, but it is not limitative. An alternative configuration is to provide a magnetic part serving as the engagement part of the push part 95 closer to the attaching part 82 to hold the blade 21 (the blade unit 20) by magnetic force. The magnetic force of the magnetic part is determined to allow disengagement at the push-down of the pressing part 92.

Figure 14:
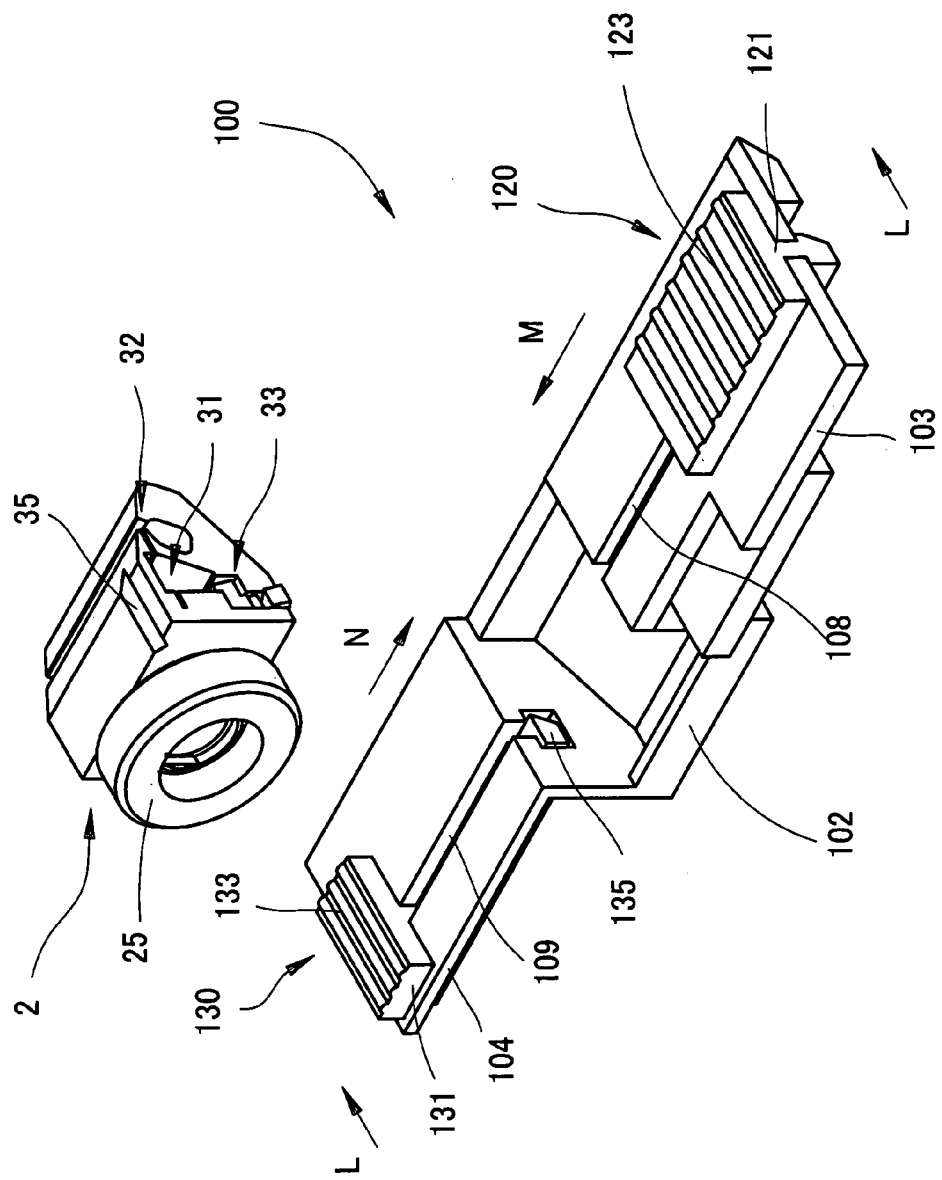
FIG. 14 is a schematic configuration view of another modified form of the blade case.
Figure 15:
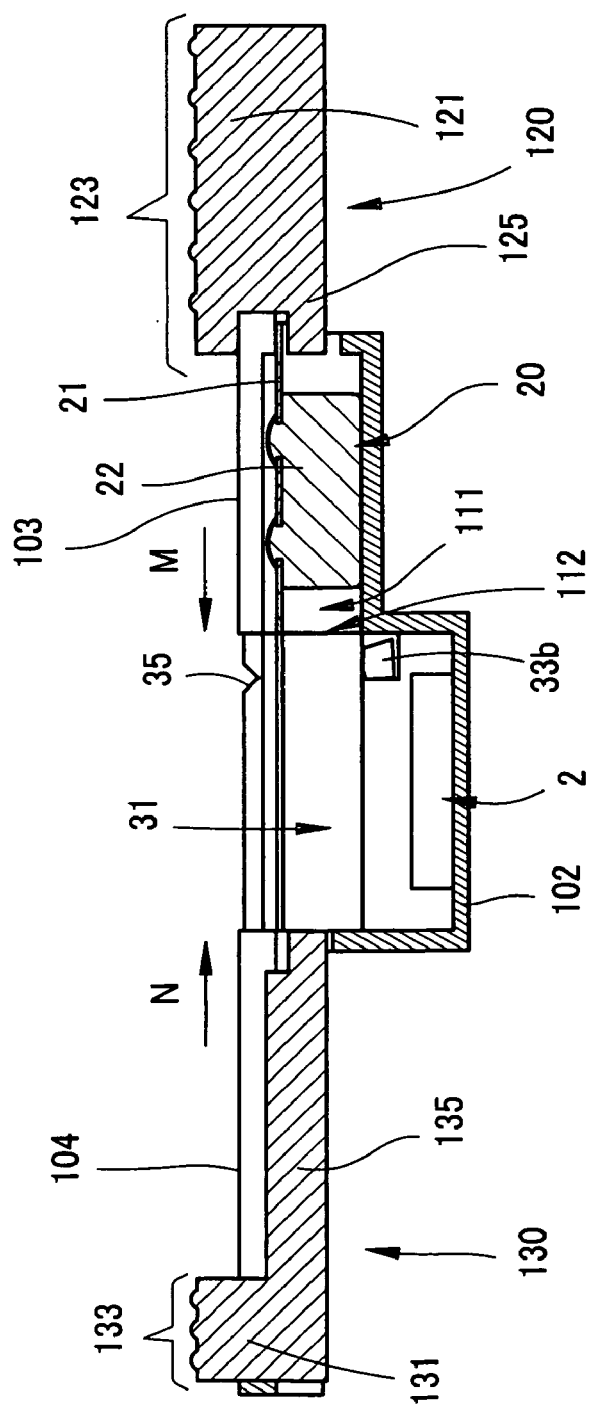
FIG. 15 is a view showing an operation to mount the blade unit from the latter modified form of the blade case to the cutter head unit.

A modified form (a third embodiment) of the blade case of the present invention will be explained below. FIG. 14 is an oblique perspective view of a blade case 100 of the third embodiment, showing a state where the blade unit 20 is stored. FIG. 15 is a sectional view showing a state where the blade unit 20 is to be inserted from the blade case 100 into the cutter head unit 2, seen from a direction of an arrow L in FIG. 14. The blade case 100 is provided, in almost the center, with an attaching part 102 for attachment of the cutter head unit 2. A first part 103 of the blade case 100 on one side of the attaching part 102 is provided with a cavity (a blade unit storing part) 111 for storing the blade unit 20 and a first push member 120 for pushing the blade unit 20 out of the cavity 111 through an opening 112. Further, a second part 104 of the blade case 100 on the other side of the attaching part 102 is provided with a second push member 130 for pushing the blade unit 20 back into the cavity 111 through the opening 112.

The first push member 120 includes a base 121, a non-flat grip surface 123 with ribs on the upper part of the base 121, and a push part (a push rod) 125 formed in the lower part of the base 121 closer to the attaching part 102.

In the upper part of the part 103, a guide groove 108 is formed extending perpendicular to the opening 112. The lower part of the base 121 is shaped to be engageable with the guide groove 108 along which the first push member 120 is movable in a direction of an arrow M. The push part 125 is of a cross section shaped to insert into the cavity 31 of the cutter head unit 2.

The second push member 130 includes a base 131, a non-flat grip surface 133 with ribs on the upper part of the base 131, and a push part (a push rod) 135 formed in the lower part of the base 131.

In the upper part of the part 104, a guide groove 109 is formed extending perpendicular to the opening 112. The lower part of the base 131 is shaped to be engageable with the guide groove 109 along which the second push member 130 is movable in a direction of an arrow N. The push part 135 is of a cross section shaped to insert into the cavity 31 of the cutter head unit 2.

The attaching part 102 is further provided with a pressing part not shown which will act on the move member 33b as with the aforementioned pressing parts 56 and 86. In the opening 112 of the cavity 111 on the ejection side, a stopper not shown is provided for preventing (restricting) the blade unit 20 from dropping or coming off (moving) as with the aforementioned stoppers 53 and 83.

When the blade unit 20 is to be transferred from the blade case 100 into the cutter head unit 2, the blade case 100 is attached (connected) to the cutter head unit 2. In this case, the cooperation between the shape of the attaching part 102 and the shape of the cutter head unit 2 brings the cavity 111 (the opening 112) of the blade case 100 into alignment with the cavity 31 (the opening 31a) of the cutter head unit 2. Further, the pressing part not shown of the attaching part 102 serves to release movement restriction imposed by the stopper 33. When the first push member 120 is moved in the direction of the arrow M, the blade unit 20 is pushed out of the cavity 111 of the blade case 100 and inserted into the cavity 31 (the opening 31a) of the cutter head unit 2. It should be noted that the blade case 100 of the third embodiment does not have to be provided with a mating part engageable with the mating part 35 of the cutter head unit 2.

When the blade unit 20 is to be returned from the cutter head unit 2 to the blade case 100, the blade case 100 is attached (connected) to the cutter head unit 2 in the same manner as at the time of insertion, the second push member 130 is moved in the direction of the arrow N, thereby pushing the blade unit 20 out of the cavity 31 of the cutter head unit 2 back into the cavity 111 of the blade case 100.

As above, the blade case 100 of the third embodiment is provided with the first push member 120 and the second push member 130. Therefore, the blade unit 20 can be mounted in and demounted from the cutter head unit 2 even when there is no engagement part such as the mating part 96 of the blade case 80 of the second embodiment with respect to the blade 61.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A corneal incision system comprising:
    a corneal incision apparatus for incising a cornea in a layered form, comprising;
    a blade unit having a blade for corneal incision; and
    a cutter head unit arranged to hold the blade unit in such a manner as to allow oscillation thereof,
    the cutter head unit including a first cavity formed with a first opening and arranged to hold the blade unit in such a manner as to allow oscillation thereof; and
    a blade case arranged to cover and internally store the blade unit, the blade case including a second cavity formed with a second opening and arranged to hold the blade unit and a restriction member for restricting movement of the blade unit within the second cavity,
    the cutter head unit and the blade case including engagement parts engageable with each other so that, under the condition that the engagements parts are engaged, the first opening and the second opening face and come close in proximity to each other to allow the blade unit to move between the first cavity of the cutter head unit and the second cavity of the blade case, and
    the blade case including a first push member for exerting insertion pressure for pushing out the blade unit held in the second cavity through the second opening against movement restriction by the restriction member in order to slide the blade unit in a lateral direction of the blade and push the blade unit out of the second cavity into the first cavity through the second opening and the first opening, the first push member being integrally held in a first straight guide of the blade case in such a manner as to be movable forward and backward in only a pushing direction, the first straight guide extending to the vicinity of the second opening, and the first push member being connected to a first operating part to be operated by operator's fingers, wherein the first push member slides the blade unit in an opposite lateral direction of the blade to pull the blade out of the first cavity and return it into the second cavity through the first opening and the second opening.

2. The corneal incision system according to claim 1, wherein the blade unit and the first push member include engagement parts engageable with each other so that the first push member can pull the blade unit out of the first cavity when the blade unit and the first push member are engaged.

3. A corneal incision system comprising:

a corneal incision apparatus for incising a cornea in a layered form, comprising;

a blade unit having a blade for corneal incision; and a cutter head unit arranged to hold the blade unit in such a manner as to allow oscillation thereof, the cutter head unit including a first cavity formed with a first opening and arranged to hold the blade unit in such a manner as to allow oscillation thereof; and a blade case arranged to cover and internally store the blade unit, the blade case including a second cavity formed with a second opening and arranged to hold the blade unit and a restriction member for restricting movement of the blade unit within the second cavity, the cutter head unit and the blade case including engagement parts engageable with each other so that, under the condition that the engagements parts are engaged, the first opening and the second opening face and come close in proximity to each other to allow the blade unit to move between the first cavity of the cutter head unit and the second cavity of the blade case, and the blade case including a first push member for exerting insertion pressure for pushing out the blade unit held in the second cavity through the second opening against movement restriction by the restriction member in order to slide the blade unit in a lateral direction of the blade and push the blade unit out of the second cavity into the first cavity through the second opening and the first opening, the first push member being integrally held in a first straight guide of the blade case in such a manner as to be movable forward and backward in only a pushing direction, the first straight guide extending to the vicinity of the second opening, and the first push member being connected to a first operating part to be operated by operator's fingers, wherein the blade case further comprises a second push member for exerting returning pressure for pushing out the blade unit held in the first cavity through the first opening in order to slide the blade unit in the lateral direction of the blade and push the blade unit out of the first cavity to return it into the second cavity through the first opening and the second opening, the second push member being integrally held in a second straight guide of the blade case in such a manner as to be movable forward and backward in only the pushing direction, and the second push member being connected to a second operating part to be operated by operator's fingers.

* * * * *